(12) United States Patent
Zhang et al.

(10) Patent No.: US 12,106,484 B2
(45) Date of Patent: Oct. 1, 2024

(54) THREE-DIMENSIONAL MEDICAL IMAGE SEGMENTATION METHOD AND SYSTEM BASED ON SHORT-TERM AND LONG-TERM MEMORY SELF-ATTENTION MODEL

(71) Applicant: HUAZHONG UNIVERSITY OF SCIENCE AND TECHNOLOGY, Hubei (CN)

(72) Inventors: Xuming Zhang, Hubei (CN); Mingwei Wen, Hubei (CN); Quan Zhou, Hubei (CN)

(73) Assignee: HUAZHONG UNIVERSITY OF SCIENCE AND TECHNOLOGY, Hubei (CN)

( * ) Notice: Subject to any disclaimer, the term of this patent is extended or adjusted under 35 U.S.C. 154(b) by 0 days.

(21) Appl. No.: 18/635,023

(22) Filed: Apr. 15, 2024

(65) Prior Publication Data
US 2024/0257356 A1 Aug. 1, 2024

Related U.S. Application Data

(63) Continuation of application No. PCT/CN2023/124989, filed on Oct. 17, 2023.

(30) Foreign Application Priority Data

Nov. 17, 2022 (CN) .......................... 202211440881.X

(51) Int. Cl.
*G06T 7/00* (2017.01)
*G06T 3/4046* (2024.01)
(Continued)

(52) U.S. Cl.
CPC .............. *G06T 7/11* (2017.01); *G06T 3/4046* (2013.01); *G06T 7/0012* (2013.01); *G06T 7/143* (2017.01);
(Continued)

(58) Field of Classification Search
CPC ....... G06T 7/11; G06T 3/4046; G06T 7/0012; G06T 7/143; G06T 2200/04;
(Continued)

(56) References Cited

U.S. PATENT DOCUMENTS

| 11,222,217 B1 * | 1/2022 | Zhang | G06F 18/214 |
| 2010/0322488 A1 * | 12/2010 | Virtue | G06T 7/11 382/128 |

(Continued)

FOREIGN PATENT DOCUMENTS

| CN | 112380949 | 2/2021 |
| CN | 113592794 | 11/2021 |

(Continued)

OTHER PUBLICATIONS

"International Search Report (Form PCT/ISA/210) of PCT/CN2023/124989," mailed on Dec. 25, 2023, pp. 1-4.
"Written Opinion of the International Searching Authority (Form PCT/ISA/237) of PCT/CN2023/124989," mailed on Dec. 25, 2023, with English translation thereof, pp. 1-9.

*Primary Examiner* — Van D Huynh
(74) *Attorney, Agent, or Firm* — JCIPRNET

(57) ABSTRACT

The disclosure belongs to the field of image segmentation in medical image processing and discloses a three-dimensional medical image segmentation method and system based on short-term and long-term memory self-attention models, in which the method can segment a target area image in the medical image, which includes the following. (1) A training set sample is established. (2) Processing is performed on the original three-dimensional medical image to be segmented to obtain a sample to be segmented. (3) A three-dimensional medical image segmentation network based on short-term and long-term memory self-attention is established and trained. (4) The sample to be segmented is input to the network, and then a segmentation result of the target area in the sample to be segmented is output. By combining CNN (Continued)

and Transformer, a new model for accurate real-time segmentation of the target area (such as a tumor) in the three-dimensional medical image is obtained.

10 Claims, 3 Drawing Sheets

(51) Int. Cl.
  *G06T 7/11* (2017.01)
  *G06T 7/143* (2017.01)
  *G16H 30/40* (2018.01)
(52) U.S. Cl.
  CPC .......... *G16H 30/40* (2018.01); *G06T 2200/04* (2013.01); *G06T 2207/20076* (2013.01); *G06T 2207/20081* (2013.01); *G06T 2207/20084* (2013.01); *G06T 2207/20132* (2013.01); *G06T 2207/30096* (2013.01)
(58) Field of Classification Search
  CPC .......... G06T 2207/20076; G06T 2207/20081; G06T 2207/20084; G06T 2207/20132; G06T 2207/30096; G16H 30/40
  See application file for complete search history.

(56) References Cited

U.S. PATENT DOCUMENTS

| | | | |
|---|---|---|---|
| 2012/0099779 A1* | 4/2012 | Gupta | G06T 7/11 382/133 |
| 2015/0279084 A1* | 10/2015 | Deuerling-Zheng | G06T 5/50 345/424 |
| 2016/0055644 A1* | 2/2016 | Betting | A61B 5/055 382/131 |
| 2016/0292847 A1* | 10/2016 | Liu | G06T 7/0012 |
| 2019/0223725 A1* | 7/2019 | Lu | G06N 3/044 |
| 2020/0085382 A1* | 3/2020 | Taerum | G06T 7/0016 |
| 2020/0380687 A1* | 12/2020 | Avital | A61B 8/5207 |
| 2021/0248751 A1* | 8/2021 | Guo | G06T 7/11 |
| 2022/0230310 A1* | 7/2022 | Xie | G06T 7/70 |
| 2022/0309674 A1* | 9/2022 | Zhang | G06T 7/11 |
| 2022/0383489 A1* | 12/2022 | Shi | G06T 7/11 |
| 2022/0384035 A1* | 12/2022 | Shi | G06V 10/774 |

FOREIGN PATENT DOCUMENTS

| | | | | |
|---|---|---|---|---|
| CN | 114187293 | | 3/2022 | |
| CN | 114519807 | | 5/2022 | |
| CN | 115147606 | | 10/2022 | |
| CN | 116129107 | | 5/2023 | |
| WO | WO-2022198050 A1 * | 9/2022 | ............... G06T 7/11 |

* cited by examiner

THREE-DIMENSIONAL MEDICAL IMAGE SEGMENTATION METHOD AND SYSTEM BASED ON SHORT-TERM AND LONG-TERM MEMORY SELF-ATTENTION MODEL

CROSS-REFERENCE TO RELATED APPLICATION

This application is a continuation of international application of PCT application serial no. PCT/CN2023/124989, filed on Oct. 17, 2023, which claims the priority benefit of China application no. 202211440881.X, filed on Nov. 17, 2022. The entirety of each of the above-mentioned patent applications is hereby incorporated by reference herein and made a part of this specification.

BACKGROUND

Technical Field

The disclosure belongs to the field of image segmentation in medical image processing, and more specifically relates to a three-dimensional medical image segmentation method and system based on a short-term and long-term memory self-attention model. The method and system are based on deep learning, especially can be used to segment a tumor area in the three-dimensional medical image.

Description of Related Art

Medical image is an important source of lesion information and has important value. Taking tumors as an example, the incidence and mortality of malignant tumors are rapidly growing worldwide, and cancer has become a significant factor threatening human health and life. Early detection and treatment is highly significant. In clinical practice, segmentation of tumors in three-dimensional medical images may provide information such as tumor measurements and localization, which contributes greatly to early diagnosis. However, because of the variations in texture and shape of tumors among different individuals, the possible occurrence of multiple tumors and blurry boundaries thereof, an efficient and accurate tumor segmentation is a highly challenging task.

Automatic segmentation of tumors in three-dimensional medical images plays a significant role in the early diagnosis and treatment of cancer. However, conventional segmentation algorithms such as thresholding, region growing, and active contour are mostly based on the differences in edge and grayscale distribution. Due to large differences in morphology, texture, and grayscale distribution of tumor images, the conventional methods have weak adaptability. For this reason, the deep learning-based image segmentation algorithms have attracted much attention in recent years, and several CNN (convolutional neural network) based models have been used for image segmentation. U-Net is currently a most commonly used network structure, and a special encoder-decoder structure thereof shows a good performance in segmentation tasks. Further research found that although the convolution-based segmentation model can effectively extract local features, the model cannot capture global features well, which influences the segmentation performance. The Transformer model originally used in natural language processing tasks can predict missing edges and reduce errors caused by noise by capturing global image features, thereby the segmentation accuracy is improved. Currently, the application of the Transformer to image processing tasks has some disadvantages. First, the Transformer requires large training samples to achieve a good performance, but it is difficult to obtain sufficient tumor images in clinical practice. Meanwhile, the amount of computation of the Transformer is large and proportional to square of the quantity of patches, which renders the training and application time-consuming in three-dimensional image segmentation tasks. In addition, the Transformer lacks the inductive bias of CNN, such as translation invariance and locality, and model performance is further limited. Since the CNN and Transformer are good at extracting local features and global features respectively, the models may be combined in different ways to improve the image segmentation performance of the model on small training samples. One method is to further optimize an attention module by adding a convolution operation to the Transformer, and another method is to combine the Transformer with CNN in the network structure.

Currently, the combined structures of CNN and Transformer used for image segmentation may be divided into three types. A first type merely uses multi-layer Transformer as the encoder, and the performance thereof is dependent on the quantity of training samples. Although the simple stacking of Transformer may improve the performance to a certain extent, the amount of computation is also significantly increased, which is not cost-effective. A second type of structure inserts the Transformer module between the CNN-based encoder and decoder for further feature extraction. The structure can merely extract global features at a low resolution and cannot fully play the role of self-attention mechanism, and the improvement in network performance is limited. A third type of structure simultaneously uses CNN and Transformer to perform dual-branch encoding and fuses encoded features of different resolutions to guide the decoding process. This parallel structure cannot effectively fuse the two models together, and the stacking of the two models causes a high computation cost.

SUMMARY

In view of the above defects or improvement needs of the existing technology, the purpose of the disclosure is to provide a three-dimensional medical image segmentation method and system based on a short-term and long-term memory self-attention (SLM-SA) model, in which by combining CNN and Transformer, a new model for accurate real-time segmentation of a target areas (such as a tumor) in the three-dimensional medical image is obtained. Learning strategies similar to memory forgetting and updating are adopted, and taking tumors as an example, the model is beneficial to improving the segmentation accuracy of complex tumors in medical images. The method uses the CNN module for preliminary extraction of image features, which effectively avoids the disadvantage of Transformer requiring a large number of samples for training. A small number of Transformer modules are used to implement the memory structure and applied to ¼ and ⅛ resolution feature maps, which effectively plays the role of the self-attention mechanism while the amount of computation is limited. The method has few parameters and a low computational complexity and may be applied to clinical practice scenarios where the real-time accurate segmentation is desired.

In order to achieve the above purpose, according to one aspect of the disclosure, a three-dimensional medical image segmentation method based on a short-term and long-term memory self-attention model is provided, which can perform segmentation on a target area image in the medical image, and includes the following.

(1) Three-dimensional medical images containing target areas and with known target area segmentation golden rules are collected, the original images are cropped according to areas of interest, and normalization processing is performed on pixel values to obtain training set samples.

(2) For an original three-dimensional medical image to be segmented, an original image is cropped according to an area of interest, and a normalization operation is performed on pixel values of the cropped image to obtain a sample to be segmented.

(3) A three-dimensional medical image segmentation network based on short-term and long-term memory self-attention is established, in which the network first uses a feature extraction module including a plurality of convolution layers, and uses a convolution calculation to convert grayscale information in a network input image into feature information to obtain initial image features. A plurality of sequentially connected convolution modules having residual structures are used to further process the initial image features to obtain corresponding convolution features. A plurality of short-term memory modules based on a multi-head self-attention mechanism is used to calculate a global correlation between the convolution features of different levels, and short-term memory features are generated based on the global correlation together with the convolution features used in the correlation calculation. A global correlation calculation is performed on all of the short-term memory features obtained by a long-term memory module also based on the multi-head self-attention mechanism to generate features to be reconstructed used to reconstruct a segmentation result, in which the long-term memory module has same structure as any one of the short-term memory modules. Finally, processing is performed on the features to be reconstructed through a plurality of convolution layers and deconvolution layers by a reconstruction module to obtain a predicted probability of a category to which each pixel of the network input image belongs to realize performing accurate segmentation on the target area in the three-dimensional medical image.

The established three-dimensional medical image segmentation network is trained by using the training set samples obtained in (1) and using the corresponding segmentation golden rules as labels, so that the trained network is able to realize performing segmentation on the target area contained in the network input image.

(4) The sample to be segmented obtained in (2) are used as the network input image to input to the trained three-dimensional medical image segmentation network based on short-term and long-term memory self-attention obtained in (3), and a segmentation result of the target area in the sample to be segmented is output.

As a further preference of the disclosure, the three-dimensional medical image segmentation network based on short-term and long-term memory self-attention established in step (3) specifically includes the following.

The feature extraction module is used to extract image features, in which the feature extraction module reduces a resolution and increases a quantity of channels through two convolution calculations with a stride of 2, the network input image is converted into a multi-channel feature map, and the initial image features are obtained.

The plurality of sequentially connected convolution modules having the residual structures are used to process the initial image features to obtain the corresponding convolution features, in which a resolution of the convolution features obtained by any one of the convolution modules is the same as a resolution of the initial image features. Preferably, the plurality of sequentially connected convolution modules having the residual structures are specifically 4 sequentially connected convolution modules having the residual structures, which are respectively recorded as the convolution module 1, the convolution module 2, the convolution module 3, and the convolution module 4, the convolution features of different levels obtained by the convolution modules are respectively recorded as the convolution feature 1, the convolution feature 2, the convolution feature 3, and the convolution feature 4.

The plurality of short-term memory modules based on the multi-head self-attention mechanism is provided, in which a quantity of the short-term memory modules is a quantity of the convolution modules having the residual structures minus 1, a first-level short-term memory module corresponds to convolution modules having residual structures of first two levels, and each subsequent level of the short-term memory modules corresponds to a convolution module having the residual structure of a next level sequentially. The first-level short-term memory module is used to calculate a correlation between convolution features obtained by the convolution modules having the residual structures of the first two levels, each subsequent level of the short-term memory module is used to calculate a correlation between short-term memory features obtained by a previous-level short-term memory module and convolution features obtained by a convolution module having the residual structure of a corresponding level, and the global correlation between all of the convolution features obtained by all of the convolution modules having the residual structures is calculated. Preferably, the plurality of short-term memory modules based on the multi-head self-attention mechanism are specifically 3 short-term memory modules based on the multi-head self-attention mechanism, the three short-term memory modules based on the multi-head self-attention mechanism are recorded as the short-term memory module 1, the short-term memory module 2, and the short-term memory module 3, and each of the short-term memory modules has two inputs. The convolution feature 1 is down-sampled and input to the short-term memory module 1 with the convolution feature 2 to obtain a short-term memory feature 1, the short-term memory feature 1 is down-sampled and input to the short-term memory module 2 with the convolution feature 3 to obtain a short-term memory feature 2, and the short-term memory feature 2 is down-sampled and input to the short-term memory module 3 with the convolution feature 4 to obtain a short-term memory feature 3.

Moreover, except for a last short-term memory module, a quantity of channels is reduced by convolution calculation for the short-term memory features obtained by each of the short-term memory modules, and is added to convolution features of a lowest level input to the short-term memory module to serve as an input of a subsequent convolution module. Preferably, a sum of the short-term memory feature 1 and the convolution feature 2 is used as an input of the convolution module 3, and a sum of the short-term memory feature 2 and the convolution feature 3 is used as an input of the convolution module 4.

The long-term memory module based on the multi-head self-attention mechanism is used to first merge the short-term memory features obtained by each of the short-term memory modules in a channel dimension to generate merged features, and then perform a global correlation calculation to generate features to be reconstructed used to reconstruct the segmentation result. Preferably, the long-term memory module based on the multi-head self-attention mechanism is used to first merge the short-term memory feature 1, the short-term memory feature 2, and the short-term memory feature 3 in the channel dimension to generate the merged features, and then a global correlation calculation is performed on the merged features to generate the features to be reconstructed used to reconstruct the segmentation result.

The reconstruction module is used to use the features to be reconstructed as the input, use the deconvolution layer with the stride of 2 to increase the image resolution, and use the two layers of convolution layers with the stride of 1 to reduce the quantity of channels, so as to finally obtain the predicted probability of the category to which each of the pixels of the network input image belongs to.

As a further preference of the disclosure, the feature extraction module has a total of 12 layers of detailed structures, and the output of the upper layer of detailed structures is used as the input of the next layer of detailed structures, which includes the following.

A first layer is a convolution layer, a stride is 2, an output resolution is ½ of the network input image, and a quantity of output channels is a preset value.

A second layer is a batch normalization (BN) layer.

A third layer is a rectified linear unit (ReLU) activation layer.

A fourth layer is a convolution layer, a stride is 1, and a resolution of input and a quantity of channels are not changed.

A fifth layer is a batch normalization (BN) layer.

A sixth layer is a rectified linear unit (ReLU) activation layer.

A seventh layer is a convolution layer, a stride is 2, and compared with the input, an output resolution is reduced by half, and a quantity of output channels is doubled.

An eighth layer is a batch normalization (BN) layer.

A ninth layer is a rectified linear unit (ReLU) activation layer.

A tenth layer is a convolution layer, a stride is 1, and a resolution of the input and a quantity of channels are not changed.

An eleventh layer is a batch normalization (BN) layer.

A twelfth layer is a rectified linear unit (ReLU) activation layer.

As a further preference of the disclosure, for any convolution module, there are 12 layers of detailed structures, and the output of the upper layer of detailed structures is used as the input of the next layer of detailed structures, which includes the following.

A first layer is a convolution layer, a stride is 1, and a resolution of input and a quantity of channels are not changed.

A second layer is a batch normalization (BN) layer.

A third layer is a rectified linear unit (ReLU) activation layer.

A fourth layer is a convolution layer, a stride is 1, and a resolution of the input and a quantity of channels are not changed.

A fifth layer is a batch normalization (BN) layer.

A sixth layer is a rectified linear unit (ReLU) activation layer, wherein an input thereof is a sum of an output of the fifth layer and an input of the first layer.

A seventh layer is a convolution layer, a stride is 1, and a resolution of the input and a quantity of channels are not changed.

An eighth layer is a batch normalization (BN) layer.

A ninth layer is a rectified linear unit (ReLU) activation layer.

A tenth layer is a convolution layer, a stride is 1, and a resolution of the input and a quantity of channels are not changed.

An eleventh layer is a batch normalization (BN) layer.

A twelfth layer is a rectified linear unit (ReLU) activation layer, wherein an input thereof is a sum of an output of the eleventh layer and an input of the seventh layer.

As a further preference of the disclosure, for the short-term memory module, the following is included.

In the input of the short-term memory module, for the first-level short-term memory module, the convolution features obtained by the convolution module having the residual structure at the first level is recorded as memory features, and the convolution features obtained by the convolution module having the residual structure at a second level is recorded as current features. For each subsequent level of the short-term memory module, the short-term memory features obtained by the previous level short-term memory module is recorded as memory features, and the convolution features obtained by the convolution module having the residual structure of a level corresponding to the short-term memory module is recorded as the current features.

For any one of the short-term memory modules, for the current features thereof, a quantity of channels is doubled through a convolution calculation before input; for the memory features thereof, a convolution calculation is performed with a stride of 2 before input, while a resolution is reduced and a quantity of channels is increased. Preferably, reducing the resolution specifically means reducing the resolution in half, and increasing the quantity of channels specifically means doubling the quantity of channels.

For any one of the short-term memory modules, the current features are regarded as Query in a self-attention calculation process, the memory features are regarded as Key and Value, so as to calculate the self-attention module in the short-term memory module, and specifically, the following is included.

First, feature coding is performed respectively on the three components, Query, Key, and Value by a convolution layer, and then obtained feature codes of Query, Key, and Value are divided into a preset quantity of patches in a spatial dimension. Then, an attention weight is calculated according to a sequence generated corresponding to Query and Key, and the formula is:

$$Attn = \text{Softmax}\left(\frac{Q \cdot K}{\sqrt{d}}\right)$$

In the formula, d is a length of a feature vector, Q and K represent a sequence corresponding to Query and Key respectively, Softmax function is applied to a dimension corresponding to the Key sequence, and Attn represents the attention weight.

Then, a quantity of groups of self-attention in the attention weight is doubled through a linear layer, input to a convolution layer to perform a convolution calculation with the resolution and quantity of channels being not changed, and then the quantity of groups of self-attention is restored by using another opposite linear layer to obtain a final attention weight. Finally, the final attention weight and Value are matrix multiplied, and then a result is restored to a three-dimensional feature map through an inverse sequence operation. For the three-dimensional feature map, learnable weights are pre-allocated according to the quantity of channels thereof, so that the channel corresponds to the learnable weight one-to-one, and then each of the channels of the three-dimensional feature map is multiplied by the corresponding learnable weight, thereby an overall output of the self-attention module is obtained. The learnable weight is able to automatically update through training.

The overall output of the self-attention module is added to the current features after being processed by a first LN (layer normalization) layer, the output is then passed through a feed-forward neural network and a second LN layer, and an obtained result is added to the output of the first LN layer to obtain the short-term memory features.

As a further preference of the disclosure, for the long-term memory module, the following is included.

First, the short-term memory features output by each of the short-term memory modules are merged in the channel dimension to obtain the merged features, the merged features are regarded as Query, Key, and Value in a self-attention calculation process, so as to calculate the self-attention module in the long-term memory module, and specifically, the following is included.

First, feature coding is performed respectively on the three components, Query, Key, and Value by a convolution layer, and then obtained feature codes of Query, Key, and Value are divided into a preset quantity of patches in a spatial dimension. Then, an attention weight is calculated according to a sequence generated corresponding to Query and Key, and the formula is:

$$Attn = \text{Softmax}\left(\frac{Q \cdot K}{\sqrt{d}}\right)$$

In the formula, d is a length of a feature vector, Q and K represent a sequence corresponding to Query and Key respectively, Softmax function is applied to a dimension corresponding to the Key sequence, and Attn represents the attention weight.

Then, a quantity of groups of self-attention in the attention weight is doubled through a linear layer, input to a convolution layer to perform a convolution calculation with the resolution and quantity of channels being not changed, and then the quantity of groups of self-attention is restored by using another opposite linear layer to obtain a final attention weight. Finally, the final attention weight and Value are matrix multiplied, and then a result is restored to a three-dimensional feature map through an inverse sequence operation. For the three-dimensional feature map, learnable weights are pre-allocated according to the quantity of channels thereof, so that the channel corresponds to the learnable weight one-to-one, and then each of the channels of the three-dimensional feature map is multiplied by the corresponding learnable weight, thereby an overall output of the self-attention module is obtained. The learnable weight is able to automatically update through training.

The overall output of the self-attention module is added to the current features after being processed by a first LN (layer normalization) layer, the output is then passed through a feed-forward neural network and a second LN layer, and an obtained result is added to the output of the first LN layer to obtain the short-term memory features.

As a further preference of the disclosure, the reconstruction module has a total of 18 layers of detail structures, and the output of the upper layer of detail structure is used as the input of the next layer of detail structure, in which the following is included.

A first layer is a batch normalization (BN) layer.

A second layer is a rectified linear unit (ReLU) activation layer.

A third layer is a convolution layer, a stride is 1, and a resolution of the input and a quantity of channels are not changed.

A fourth layer is a batch normalization (BN) layer.

A fifth layer is a rectified linear unit (ReLU) activation layer.

A sixth layer is a deconvolution layer, a stride is 2, and compared with the input, an output resolution is doubled, and a quantity of output channels is not changed.

A seventh layer is a batch normalization (BN) layer.

An eighth layer is a rectified linear unit (ReLU) activation layer.

A ninth layer is a convolution layer, a stride is 1, and a resolution of the input and a quantity of channels are not changed.

A tenth layer is a batch normalization (BN) layer.

An eleventh layer is a rectified linear unit (ReLU) activation layer.

A twelfth layer is a deconvolution layer, a stride is 2, and compared with the input, an output resolution is doubled, and a quantity of output channels is not changed.

A thirteenth layer is a batch normalization (BN) layer.

A fourteenth layer is a rectified linear unit (ReLU) activation layer.

A fifteenth layer is a convolution layer, a stride is 1, and compared with the input, an output resolution is not changed, and a quantity of output channels is reduced by half.

A sixteenth layer is a batch normalization (BN) layer.

A seventeenth layer is a rectified linear unit (ReLU) activation layer.

An eighteenth layer is a convolution layer, a stride is 1, and compared with the input, an output resolution is not changed, and a quantity of output channels is 2.

As a further preference of the disclosure, in the step (1), the training set samples further include performing rotation, translation, and/or flipping on the cropped image, and normalization processing is performed on the pixel values to obtain the samples.

The target area is a tumor area, an organ area, or a blood vessel area.

According to another aspect of the disclosure, the disclosure provides a three-dimensional medical image segmentation system based on the short-term and long-term memory self-attention model, which includes the following functional modules.

An image pre-processing function module is used to crop an original image according to an area of interest for an original three-dimensional medical image to be segmented, and perform a normalization operation on pixel values of the cropped image to obtain a sample to be segmented.

The three-dimensional medical image segmentation network based on short-term and long-term memory self-attention is used to first use a feature extraction module including a plurality of convolution layers, and use a convolution calculation to convert grayscale information in a network input image into feature information to obtain initial image features. A plurality of sequentially connected convolution modules having residual structures are used to further process the initial image features to obtain corresponding convolution features. A plurality of short-term memory modules based on a multi-head self-attention mechanism is used to calculate a global correlation between the convolution features of different levels, and short-term memory features are generated based on the global correlation together with the convolution features used in the correlation calculation. A global correlation calculation is performed on all of the short-term memory features obtained by a long-term memory module also based on the multi-head self-attention mechanism to generate features to be reconstructed used to reconstruct a segmentation result, in which the long-term memory module has same structure as any one of the short-term memory modules. Finally, processing is performed on the features to be reconstructed through a plurality of convolution layers and deconvolution layers by a reconstruction module to obtain a predicted probability of a category to which each pixel of the network input image belongs to realize performing accurate segmentation on the target area in the three-dimensional medical image.

The three-dimensional medical image segmentation network based on short-term and long-term memory self-attention has been trained to use the sample to be segmented obtained from the image pre-processing function module as the network input image to input, and output the segmentation result of the target area in the sample to be segmented, in which the training is performed by using the training set samples and using corresponding segmentation golden rules as labels, and the training set samples are obtained by collecting three-dimensional medical images containing target areas and with known target area segmentation golden rules, cropping the original images according to areas of interest, and performing normalization processing on pixel values.

As a further preference of the disclosure, the three-dimensional medical image segmentation network based on short-term and long-term memory self-attention specifically includes the following.

The feature extraction module is used to extract image features, in which the feature extraction module reduces a resolution and increases a quantity of channels through two convolution calculations with a stride of 2, the network input image is converted into a multi-channel feature map, and the initial image features are obtained.

The plurality of sequentially connected convolution modules having the residual structures are used to process the initial image features to obtain the corresponding convolution features, in which a resolution of the convolution features obtained by any one of the convolution modules is the same as a resolution of the initial image features. Preferably, the plurality of sequentially connected convolution modules having the residual structures are specifically 4 sequentially connected convolution modules having the residual structures, which are respectively recorded as the convolution module 1, the convolution module 2, the convolution module 3, and the convolution module 4, the convolution features of different levels obtained by the convolution modules are respectively recorded as the convolution feature 1, the convolution feature 2, the convolution feature 3, and the convolution feature 4.

The plurality of short-term memory modules based on the multi-head self-attention mechanism is provided, in which a quantity of the short-term memory modules is a quantity of the convolution modules having the residual structures minus 1, a first-level short-term memory module corresponds to convolution modules having residual structures of first two levels, and each subsequent level of the short-term memory modules corresponds to a convolution module having the residual structure of a next level sequentially. The first-level short-term memory module is used to calculate a correlation between convolution features obtained by the convolution modules having the residual structures of the first two levels, each subsequent level of the short-term memory module is used to calculate a correlation between short-term memory features obtained by a previous-level short-term memory module and convolution features obtained by a convolution module having the residual structure of a corresponding level, and the global correlation between all of the convolution features obtained by all of the convolution modules having the residual structures is calculated. Preferably, the plurality of short-term memory modules based on the multi-head self-attention mechanism are specifically 3 short-term memory modules based on the multi-head self-attention mechanism, the three short-term memory modules based on the multi-head self-attention mechanism are recorded as the short-term memory module 1, the short-term memory module 2, and the short-term memory module 3, and each of the short-term memory modules has two inputs. The convolution feature 1 is down-sampled and input to the short-term memory module 1 with the convolution feature 2 to obtain a short-term memory feature 1, the short-term memory feature 1 is down-sampled and input to the short-term memory module 2 with the convolution feature 3 to obtain a short-term memory feature 2, and the short-term memory feature 2 is down-sampled and input to the short-term memory module 3 with the convolution feature 4 to obtain a short-term memory feature 3.

Moreover, except for a last short-term memory module, a quantity of channels is reduced by convolution calculation for the short-term memory features obtained by each of the short-term memory modules, and is added to convolution features of a lowest level input to the short-term memory module to serve as an input of a subsequent convolution module. Preferably, a sum of the short-term memory feature 1 and the convolution feature 2 is used as an input of the convolution module 3, and a sum of the short-term memory feature 2 and the convolution feature 3 is used as an input of the convolution module 4.

The long-term memory module based on the multi-head self-attention mechanism is used to first merge the short-term memory features obtained by each of the short-term memory modules in a channel dimension to generate merged features, and then perform a global correlation calculation to generate features to be reconstructed used to reconstruct the segmentation result. Preferably, the long-term memory module based on the multi-head self-attention mechanism is used to first merge the short-term memory feature 1, the short-term memory feature 2, and the short-term memory feature 3 in the channel dimension to generate the merged features, and then a global correlation calculation is performed on the merged features to generate the features to be reconstructed used to reconstruct the segmentation result.

The reconstruction module is used to use the features to be reconstructed as the input, use the deconvolution layer with the stride of 2 to increase the image resolution, and use the two layers of convolution layers with the stride of 1 to reduce the quantity of channels, so as to finally obtain the predicted probability of the category to which each of the pixels of the network input image belongs to.

Through the above technical solutions conceived by the disclosure, compared with the related art, taking the tumor area as the target area as an example, the following beneficial effects can be achieved.

1. This disclosure combines the advantages of both CNN and Transformer models and proposes a short-term and long-term memory self-attention structure, which improves the segmentation accuracy of the tumor areas in the three-dimensional medical images, thereby the interference of similar areas is effectively eliminated and completeness and accuracy of detection of multiple tumors are improved. The disclosure uses the CNN module to perform preliminary extraction of image features, which overcomes the inherent shortcomings of the Transformer model and can obtain a good segmentation effect of tumors on data sets with a small sample size.

2. The model in the disclosure minimizes module stacking and model merging that are not helpful in improving accuracy, the model parameters are less and the computational complexity is low, thereby the speed of automatic segmentation of tumors in three-dimensional medical images is improved, which is suitable for application scenarios with a high requirement on the real-time property.

DESCRIPTION OF THE EMBODIMENTS

Figure 1:
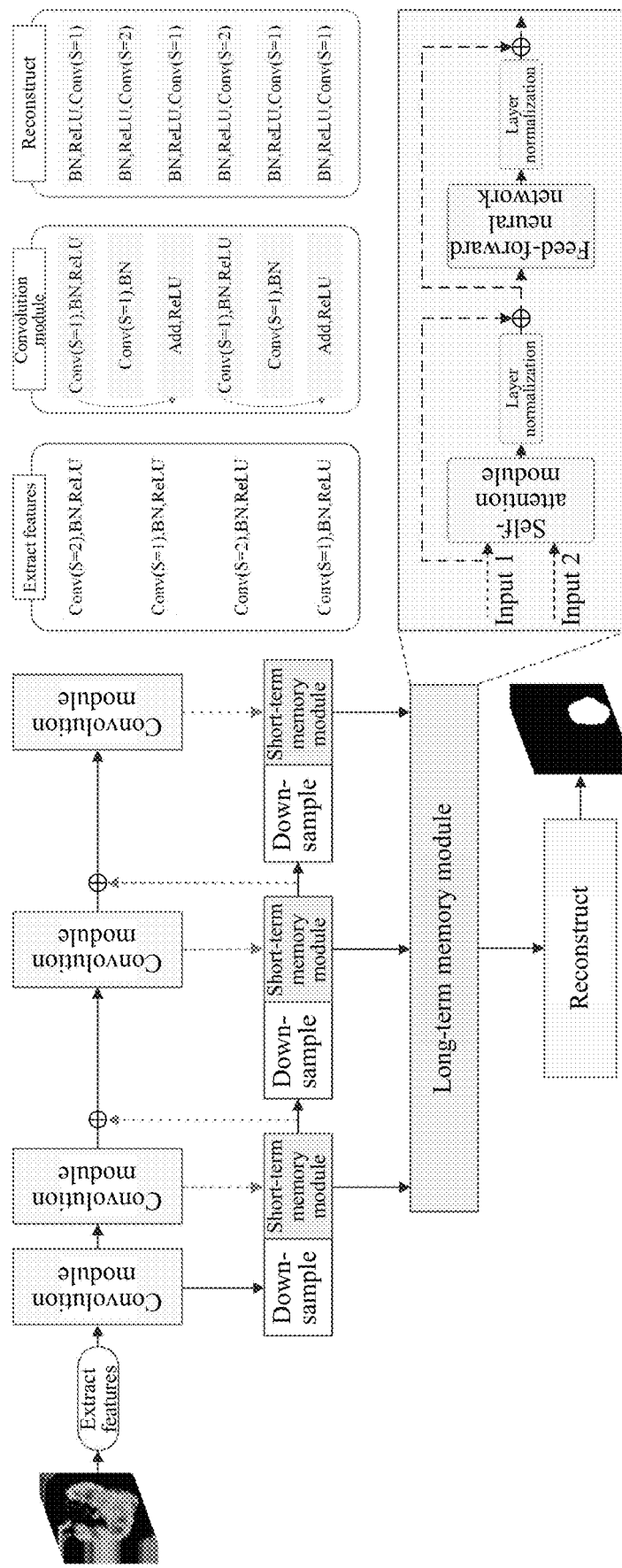
FIG. 1 is a schematic diagram of an overall structure of a deep learning model according to an embodiment of the disclosure.

In order to make the purpose, technical solutions, and advantages of the disclosure more clear, the disclosure will be further described in detail below with reference to the accompanying drawings and embodiments. It should be understood that the specific embodiments described here is merely used to illustrate the disclosure rather than to limit the disclosure. In addition, the technical features involved in the various embodiments of the disclosure described below may be combined with each other as long as no conflicts present between each other.

The disclosure combines deep learning with short-term and long-term memory self-attention model (SLM-SA) to obtain a three-dimensional medical image segmentation method for a tumor area. In SLM-SA, an improved self-attention module is constructed based on Transformer to mine the correlation between different levels and local features extracted by CNN (convolutional neural network). At the same time, a short-term and long-term memory structure is designed to filter and combine the correlation between the multiple layers and the features to achieve the elimination of similar areas and the accurate detection of multiple tumors. Combining feature extraction based on the multi-layer convolutional neural network and an image reconstruction module, accurate segmentation of the tumor area in the three-dimensional medical image is achieved.

The three-dimensional medical image segmentation network based on short-term and long-term memory self-attention corresponds to the following. First, the three-dimensional medical image segmentation network uses a feature extraction module comprising multiple convolution layers, and grayscale information in the image is converted into feature information by using convolution calculation to obtain an initial image feature. Then, multiple convolution modules with residual structures are used to further process the initial image feature to obtain a convolution feature containing high-level semantic information. Then, a short-term memory module based on a multi-head self-attention mechanism is used to mine a global correlation between different levels of convolution features, a short-term memory feature is generated based on the correlation combining with the convolution feature used in the correlation calculation, and each calculation is equivalent to performing a forgetting and updating of memory while combining the relationship between current knowledge and information of a deep level. Afterward, a long-term memory module also based on the multi-head self-attention mechanism performs a global self-attention calculation on all short-term memory features input, and then features to be reconstructed used to reconstruct a segmentation result is generated while combining the semantic information in all obtained short-term memory features, in which the short-term memory module and the long-term memory module have the same structure. Finally, the reconstruction module gradually restores the resolution of the image through multiple convolution layers and deconvolution layers and reduce a quantity of channels, a predicted probability of a category to which each pixel belongs is obtained, and accurate segmentation of a target area in the three-dimensional medical image is achieved.

Figure 2:
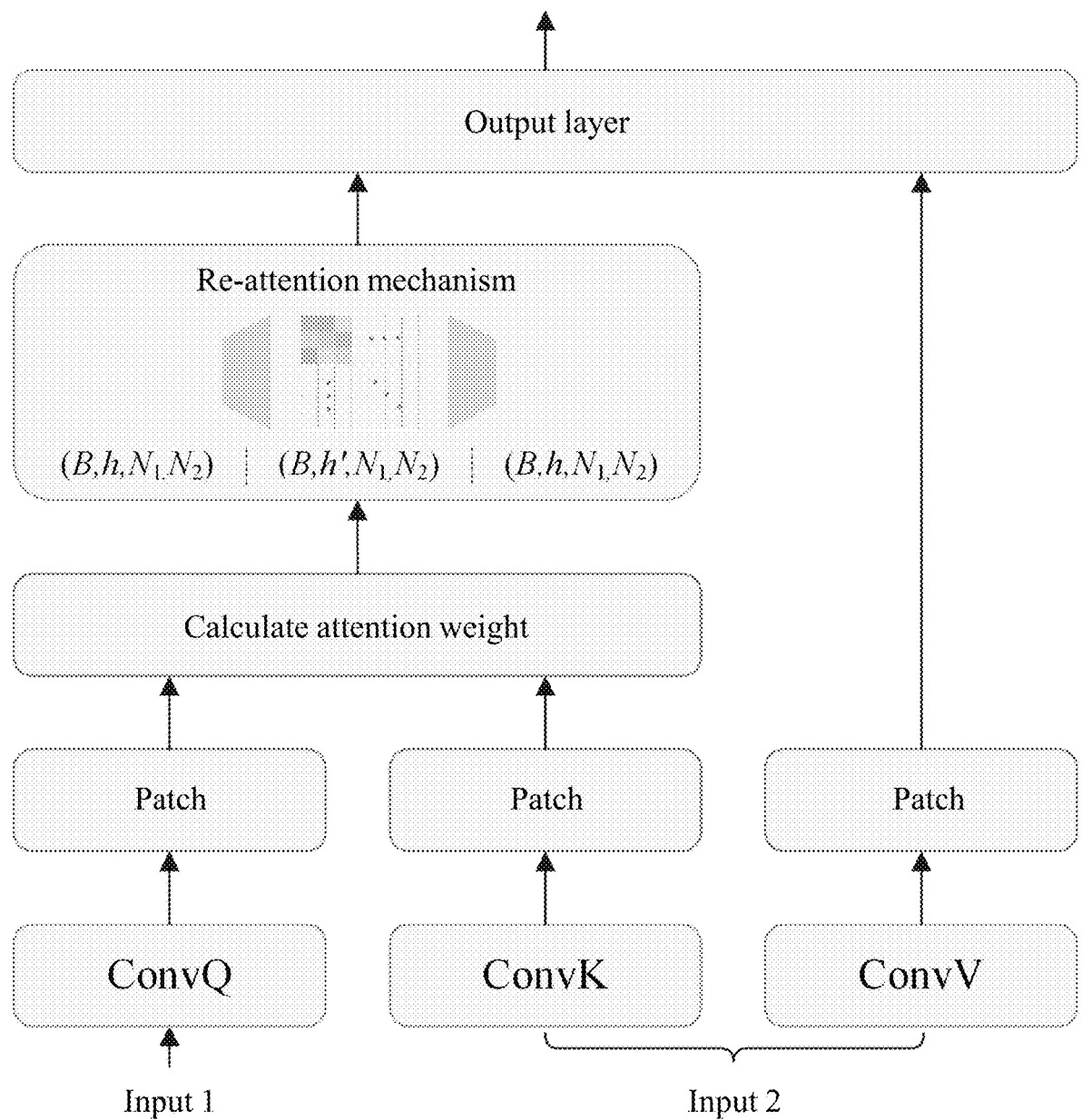
FIG. 2 is a schematic diagram of a structure of a self-attention module according to an embodiment of the disclosure.

Specifically, the following is as shown in FIG. 1 and FIG. 2 (FIG. 1 is a schematic diagram of an overall structure of a deep learning model according to an embodiment of the disclosure, and FIG. 2 is a schematic diagram of a structure of a self-attention module according to an embodiment of the disclosure).

First, the feature extraction module is used to extract image features, in which by two convolution calculations with a stride of 2, the resolution is reduced, and the quantity of channels is increased. The medical image is converted into a multi-channel feature map, and initial image features are obtained.

Then, the initial image feature is processed through repeated convolution modules, the output of the previous convolution module is used as the input of the next convolution module, while the resolution of the feature map remains unchanged. For example, the model includes 4 convolution modules, and convolution features 1 to 4 are obtained respectively.

After obtaining the convolution features of multiple levels, the short-term memory module based on the multi-head self-attention mechanism is used to mine a global correlation between the convolution features of different levels, and short-term memory features are generated based on the correlation combining with the convolution features used in the correlation calculation. For example, the model includes three short-term memory modules, each of the short-term memory modules has two inputs. A short-term memory feature 1 is obtained after a convolution feature 1 is downsampled and input with a convolution feature 2 to a short-term memory module 1, a short-term memory feature 2 is obtained after the short-term memory feature 1 is downsampled and input with a convolution feature 3 to a short-term memory module 2, and a short-term memory feature 3 is obtained after the short-term memory feature 2 is downsampled and input with a convolution feature 4 to a short-term memory module 3. Except for the short-term memory module of the last level, convolution calculation is performed to reduce the quantity of channels for the short-term memory feature obtained by each short-term memory module, and the feature is added to the convolution feature input to the short-term memory module to serve as the input of the convolution module of the next level. As in the above example, the short-term memory feature 1 is added to the convolution feature 2 to serve as the input of the convolution module 3, and the short-term memory feature 2 is added to the convolution feature 3 to serve as the input of the convolution module 4.

After the calculation of the short-term memory module is completed, the obtained short-term memory features 1 to 3 are merged in the channel dimension to generate a merged feature, and the merged feature is input into the long-term memory module based on the multi-head self-attention mechanism. The long-term memory module performs a global self-attention calculation to combine the semantic information in all obtained short-term memory features to generate features to be reconstructed used to reconstruct a segmentation result.

Finally, the features to be reconstructed are input into the reconstruction module, in which a deconvolution layer with a stride of 2 is used to increase the resolution of the image, and the last two convolution layers with a stride of 1 are used to reduce the quantity of channels. Finally, the predicted probability of the category to which each pixel belongs is obtained, that is, the segmentation result of the target area in the medical image.

The feature extraction module has a total of 12 layers of detail structures, and the output of the upper layer of the detail structure is used as the input of the next layer of the detail structure, which are described as follows.

A first layer is a convolution layer, the stride is 2, the output resolution is ½ of the original image, and the quantity of output channels is a preset value. A second layer is a batch normalization (BN) layer. A third layer is a rectified linear unit (ReLU) activation layer. A fourth layer is a convolution layer, the stride is 1, while the resolution and quantity of channels are not changed. A fifth layer is a BN layer. A sixth layer is a ReLU activation layer. A seventh layer is a convolution layer, the stride is 2, the output resolution is reduced by half, and the quantity of output channels is doubled. An eighth layer is a BN layer. A ninth layer is a ReLU activation layer. A tenth layer is a convolution layer, the stride is 1, while the resolution and quantity of channels are not changed. An eleventh layer is a BN layer. A twelfth layer is a ReLU activation layer.

Any one of the convolution module has a total of 12 layers of detail structures, and the output of the upper layer of the detail structure is used as the input of the next layer of the detail structure, which are described as follows. A first layer is a convolution layer, the stride is 1, and the resolution and quantity of channels are not changed. A second layer is a BN layer. A third layer is a ReLU activation layer. A fourth layer is a convolution layer, the stride is 1, and the resolution and quantity of channels are not changed. A fifth layer is a BN layer. A sixth layer is a ReLU activation layer. The output of the fifth layer is first added to the input of the first layer and then serves as the input of the sixth layer. The seventh layer is a convolution layer, the stride is 1, and the resolution and quantity of channels are not changed. An eighth layer is a BN layer. A ninth layer is a ReLU activation layer. A tenth layer is a convolution layer, the stride is 1, and the resolution and quantity of channels are not changed. An eleventh layer is a BN layer. A twelfth layer is a ReLU activation layer. The output of the eleventh layer is first added to the input of the seventh layer and then serves as the input of the twelfth layer.

For the short-term memory module, the module is specifically as follows. In the input of the short-term memory module, convolution features 2 to 4 is recorded as current features, convolution feature 1 and short-term memory features 1 to 2 are recorded as memory features. For the current feature, the quantity of channels is doubled through a convolution calculation before input. For the memory feature, a convolution calculation with a stride of 2 is performed before input, and the resolution of the feature map is reduced to ⅛ of the original image to reduce the amount of calculation and speed up the inference process. Also, the quantity of channels is doubled to retain enough feature information.

In the short-term memory module, the current feature is regarded as Query in the self-attention calculation process, and the memory features are regarded as Key and Value to calculate the self-attention module in the short-term memory module. The calculation is described as follows.

First, feature coding is performed respectively on the three components, Query, Key, and Value, by a convolution layer. Afterward, obtained feature codes of Query, Key, and Value are divided into a preset quantity of patches in the spatial dimension. Next, the attention weight is calculated according to the sequence generated corresponding to Query and Key. The formula is:

$$Attn = \text{Softmax}\left(\frac{Q \cdot K}{\sqrt{d}}\right)$$

In the formula, d is the length of the feature vector, Q and K represent the sequence corresponding to Query and Key respectively, the Softmax function is applied to the dimension corresponding to the Key sequence, and Attn represents the attention weight.

Then, a quantity of groups of self-attention in the attention weight is doubled through a linear layer, input to a convolution layer to perform a convolution calculation with the resolution and quantity of channels being not changed, and then the quantity of groups of self-attention is restored by using another opposite linear layer to obtain a final attention weight. Finally, the final attention weight and Value are matrix multiplied, and then the result is restored to a three-dimensional feature map through the inverse sequence operation. For the three-dimensional feature map, a learnable weight is pre-allocated according to the quantity of channels thereof, so that the channel corresponds to the learnable weight one-to-one, and then each channel of the three-dimensional feature map is multiplied by the corresponding learnable weight, thereby the overall output of the self-attention module is obtained. The learnable weight may be automatically updated through training.

The overall output of the self-attention module is added to the current features after being processed by a first LN (layer normalization) layer. Then, the output is passed through a feed-forward neural network and a second LN layer, and the obtained result is added to the output of the first LN layer to obtain the short-term memory feature.

For the long-term memory module, the module is specifically as follows. The short-term memory features output by each short-term memory module are merged in the channel dimension to obtain the merged features. The merged features are regarded as the Query, Key, and Value in the self-attention calculation process to perform the calculation of the self-attention module in the long-term memory module. The calculation is described as follows.

First, feature coding is performed respectively on the three components, Query, Key, and Value, by a convolution layer. Afterward, obtained feature codes of Query, Key, and Value are divided into a preset quantity of patches in the spatial dimension. Next, the attention weight is calculated according to the sequence generated corresponding to Query and Key. The formula is:

$$Attn = \text{Softmax}\left(\frac{Q \cdot K}{\sqrt{d}}\right)$$

In the formula, d is the length of the feature vector, Q and K represent the sequence corresponding to Query and Key respectively, the Softmax function is applied to the dimension corresponding to the Key sequence, and Attn represents the attention weight.

Then, a quantity of groups of self-attention in the attention weight is doubled through a linear layer, input to a convolution layer to perform a convolution calculation with the resolution and quantity of channels being not changed, and then the quantity of groups of self-attention is restored by using another opposite linear layer to obtain a final attention weight. Finally, the final attention weight and Value are matrix multiplied, and then the result is restored to a three-dimensional feature map through the inverse sequence operation. For the three-dimensional feature map, a learnable weight is pre-allocated according to the quantity of channels thereof, so that the channel corresponds to the learnable weight one-to-one, and then each channel of the three-dimensional feature map is multiplied by the corresponding learnable weight, thereby the overall output of the self-attention module is obtained. The learnable weight may be automatically updated through training.

The overall output of the self-attention module is added to the self-attention module after being processing by the first LN (layer normalization) layer. Then, the output is passed through the feed-forward neural network and the second LN layer, the obtained result is added to the output of the first LN layer to obtain the long-term memory feature, and the long-term memory feature is used as the input of the reconstruction module.

The reconstruction module has a total of 18 layers of detail structures, and the output of the upper layer of the detail structure is used as the input of the next layer of the detail structure, which are described as follows. A first layer is a BN (batch normalization) layer. A second layer is a ReLU (rectified linear unit) activation layer. A third layer is a convolution layer, the stride is 1, and the resolution and quantity of channels are not changed. A fourth layer is a BN layer. A fifth layer is a ReLU activation layer. A sixth layer is a deconvolution layer, the stride is 2, the resolution is doubled, and the quantity of channels is not changed. A seventh layer is a BN layer. An eighth layer is a ReLU activation layer. A ninth layer is a convolution layer, the stride is 1, and the resolution and quantity of channels are not changed. A tenth layer is a BN layer. An eleventh layer is a ReLU activation layer. A twelfth layer is a deconvolution layer, the stride is 2, the resolution is doubled, and the quantity of channels is not changed. A thirteenth layer is a BN layer. A fourteenth layer is a ReLU activation layer. A fifteenth layer is a convolution layer, the stride is 1, the resolution is not changed, and the quantity of channels is reduced by half. A sixteenth layer is a BN layer. A seventeenth layer is a ReLU activation layer. An eighteenth layer is a convolution layer, the stride is 1, the resolution is not changed, and the quantity of output channels is 2. The segmentation result of the target area in the medical image is obtained.

Certainly, the feature extraction module, the convolution module having the residual structure, and the reconstruction module may also be established with reference to related art.

In addition, the network may use the sum of cross entropy and Dice as the loss function to train the model. The formula is as follows:

$$L_f = \frac{a}{N} \times \sum_{j=1}^{N}(1 - \text{Dice}_j) + (1 - a) \times L_{CrossEntropy}$$

$$\text{Dice} = \frac{2 \cdot TP}{(TP + FP) + (TP + FN)}$$

$$L_{CrossEntropy} = -\frac{1}{M}\sum_{i}^{M}\sum_{c=1}^{N} y_{ic}\log(p_{ic})$$

In the formula, TP, FN, and FP are quantities of true positive, false negative, and false positive pixels respectively, N represents the quantity of segmented categories, and M represents the total quantity of samples. If the true category of sample i is c, 1 is taken for $y_{ic}$, otherwise 0 is taken. $p_{ic}$ is the predicted probability that sample i belongs to category c, and 0.5 is taken for a.

A medical image of a size of 96×96×96 (the unit of each dimension value is pixel; same for below) is taken as an example. FIG. 1 is a schematic diagram of an overall structure of a deep learning model according to an embodiment of the disclosure. The calculation process thereof is applied to the three-dimensional medical image to obtain an accurate segmentation result of a tumor area. Specifically, the process includes the following.

1. The input image of the size of 1×96×96×96 is calculated by the feature extraction module to obtain a feature map of 32×24×24×24. Subsequently, the input and output feature maps of each convolution module have the same size.
2. For the calculation of the short-term memory module at each stage, the size of the memory feature is changed from 32×24×24×24 to 64×12×12×12 through convolution calculation, the channels of the current feature are expanded through convolution calculation, and the size is changed from 32×24×24×24 to 64×24×24×24. The output size of the short-term memory module is 64×24×24×24. Through convolution calculation, the channel size is reduced and the size is changed to 32×24×24×24 to obtain the final output. The output is simultaneously added to the current feature as an update.
3. The output of each short-term memory module is merged in the channel dimension to obtain the input of the long-term memory module, the size is 96×24×24×24, and the output size is the same.
4. The reconstruction module gradually obtains a category prediction probability matrix of 2×96×96×96 through convolution calculation from the feature map of the size of 96×24×24×24, which is the segmentation result.

FIG. 2 is a schematic diagram of a structure of a self-attention module according to an embodiment of the disclosure. Input feature maps with sizes of 64×24×24×24 (input 1) and 64×12×12×12 (input 2) are taken for examples, respectively, including the following.
1. Corresponding convolution calculation and coding operation with a patch size of 2×2×2 and an attention head quantity of 4 are used respectively. Query is obtained from the input 1 with a size of 4×1728×128, and Key and Value are obtained from the input 2 with a size of 4×216×128.
2. Query and Key are matrix multiplied, a weight map is obtained, and the size is 4×1728×216. Then, calculation of Reattention is performed, and the size is not changed.
3. The weight map and Value are matrix multiplied, and then the features are restored to the format of the three-dimensional feature map. Each channel is multiplied by a learnable parameter, and the size of the output feature map is 64×24×24×24.

Embodiment 1

Based on the method, segmentation processing is performed on an actual three-dimensional medical image, which specifically includes the following.
(1) The KiTS19 data set is used, left and right kidneys of each sample are separated, and merely data containing tumors is retained. A total of 215 kidney images of 96×96×96 are obtained. Binary labels of containing merely tumor and non-tumor are generated according to kidney segmentation labels provided. Through data augmentation including rotation, translation, and flipping, 5375 samples are obtained, in which 4350, 525, and 500 samples are used for training, validation, and testing respectively.
(2) The training set and validation set are used to train the model proposed by the disclosure, optimal model parameters are loaded and applied to the test set, the predicted results of the tumor areas in the images are output, and finally a quantitative evaluation of the segmentation result is conducted.

Furthermore, in order to verify the method according to the disclosure, comparative examples are designed as follows (each comparative example also uses the KiTS19 data set).

Comparative Example 1

U-Net is used (U-Net: convolutional networks for biomedical image segmentation. In: Proceedings of the eighteenth International Conference on Medical Image Computing and Computer-Assisted Intervention, 234-241, 2015) to implement the segmentation task of the tumor area in the three-dimensional medical image. The data set, learning rate, quantity of iterations, and optimizer parameters the same as the method of the disclosure are used for training.

Comparative Example 2

Attention U-Net is used (Batch target recognition count under complex conditions based on att-unet. In: Proceedings of the fifth International Conference on Computer and Communication Systems, 261-265, 2020) to implement the segmentation task of the tumor area in the three-dimensional medical image. The data set, learning rate, quantity of iterations, and optimizer parameters the same as the method of the disclosure are used for training.

Comparative Example 3

UNet++ is used (Unet plus plus: a nested u-net architecture for medical image segmentation. Deep Learning in Medical Image Analysis and Multimodal Learning for Clinical Decision Support 11045, 3-11, 2018) to implement the segmentation task of the tumor area in the three-dimensional medical image. The data set, learning rate, quantity of iterations, and optimizer parameters the same as the method of the disclosure are used for training.

Comparative Example 4

TransBTS is used (TransBTS: multimodal brain tumor segmentation using transformer. In: Proceedings of the International Conference on Medical Image Computing and Computer Assisted Intervention, 109-119, 2021) to implement the segmentation task of the tumor area in the three-dimensional medical image. The data set, learning rate, quantity of iterations, and optimizer parameters the same as the method of the disclosure are used for training.

Comparative Example 5

UNETR is used (UNETR: transformers for 3D medical image segmentation. In: Proceedings of the IEEE/CVF Winter Conference on Applications of Computer Vision, 1748-1758, 2022) to implement the segmentation task of the tumor area in the three-dimensional medical image. The data set, learning rate, quantity of iterations, and optimizer parameters the same as the method of the disclosure are used for training.

Result Analysis

In order to reflect the advantages of the disclosure, the segmentation effect of Embodiment 1 is compared with Comparative Examples 1 to 5. Evaluation is performed by using Dice coefficient, intersection over union (IOU), 95% Hausdorff Distance (HD95), and relative volume error (RVE) for quantitative comparison. The definitions of IOU, HD95, and RVE are as follows:

$$IoU = \frac{TP}{TP + FP + FN}$$

$$HD95 = \max{}_{k95\%}[d(X, Y), d(Y, X)]$$

$$d(X, Y) = \left\{\min_{y \in Y} \|x - y\| | x \in X\right\}, d(Y, X) = \left\{\min_{x \in X} \|y - x\| | y \in Y\right\}$$

$$RVE(R_a, R_b) = \frac{\text{abs}(|R_a| - |R_b|)}{|R_b|}$$

In the formula, min is the calculated minimum value, $\max_{k95\%}$ represents that the maximum value of the 9fifth percentile is taken, abs represents the calculated absolute value, $|R_a|$ and $|R_b|$ represent the volumes of area $R_a$ and $R_b$ respectively.

In Table 1, the four quantitative evaluation indicators of segmentation results of Embodiment 1 and Comparative Examples 1 to 5 are listed, as well as the running speed, computational complexity, and parameter size. It may be seen from the table, compared Comparative Examples 1 to 5, Embodiment 1 has significant improvements in the four quantitative evaluation indicators of Dice, IoU, HD95, and RVE. At the same time, the parameter size is merely 0.871M and the computational complexity is merely 52G. 82.4% of Dice is achieved at 55 frames per second (FPS), and an accurate real-time segmentation of the tumor in the three-dimensional medical image is achieved.

TABLE 1

Segmentation accuracy of each segmentation method in KiTS19

| Model | Dice | IoU | HD95 (mm) | RVE | FPS | FLOPs | Parameters |
|---|---|---|---|---|---|---|---|
| SLM-SA | 0.824 | 0.725 | 10.66 | 0.241 | 55 | 52 G | 0.871M |
| U-Net | 0.755 | 0.668 | 13.42 | 0.273 | 236 | 1076 G | 98.74M |
| Att-Unet | 0.761 | 0.676 | 11.54 | 0.270 | 155 | 1082 G | 99.08M |
| UNet++ | 0.734 | 0.640 | 19.03 | 0.757 | 2 | 1779 G | 58.93M |
| TransBTS | 0.766 | 0.677 | 11.89 | 0.278 | 70 | 1025 G | 106.3M |
| UNETR | 0.531 | 0.447 | 29.89 | 2.524 | 57 | 879 G | 139.6M |

Figure 3:
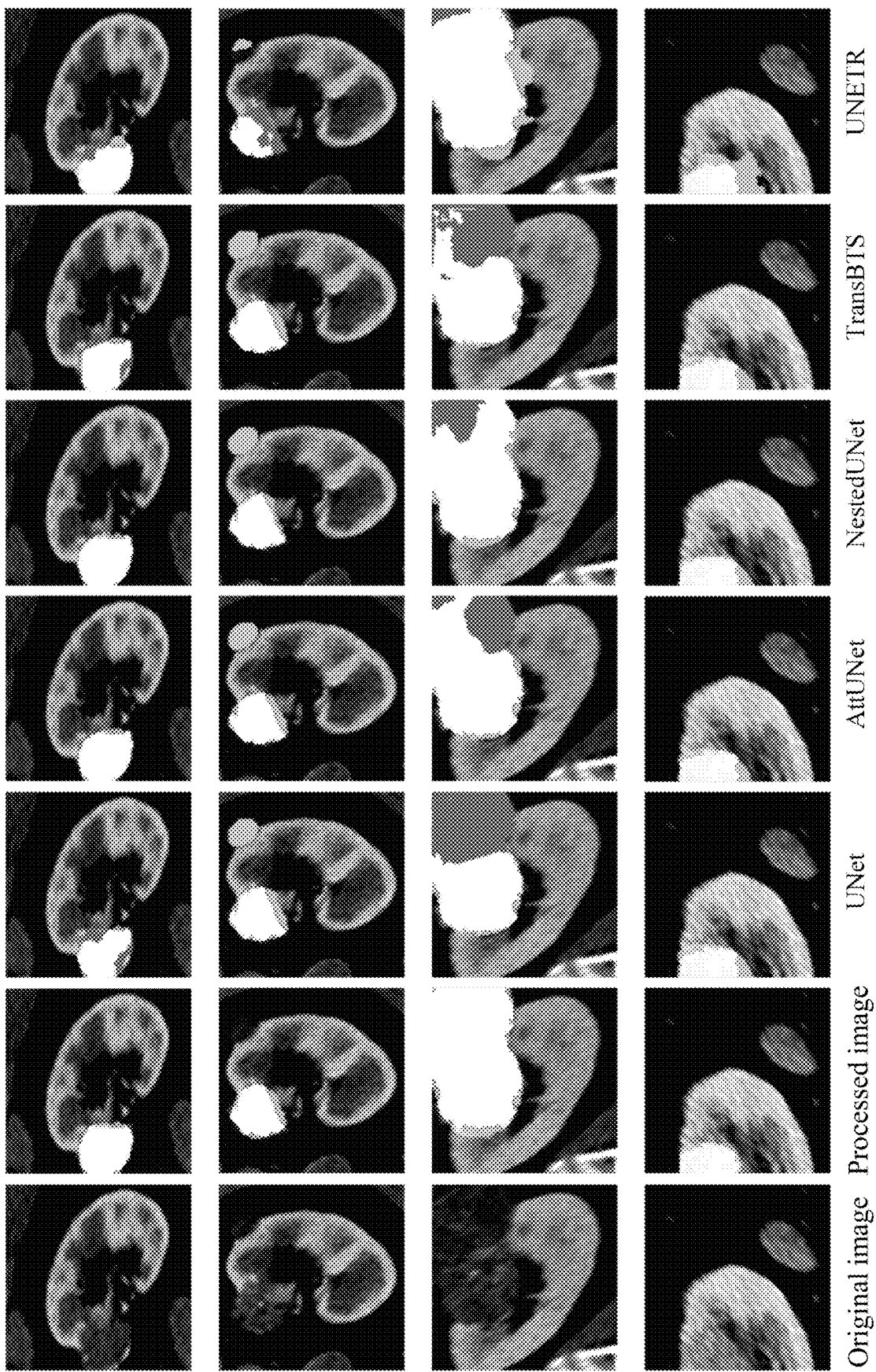
FIG. 3 shows visual effect diagrams of segmentation images corresponding to Embodiment 1 and Comparative Examples 1 to 5, in which small pictures in rows from left to right correspond sequentially to original image, after processing by Embodiment 1 (our method), after processing by Comparative Example 1 (UNet), after processing by Comparative Example 2 (Attention UNet, that is AttUNet), after processing by Comparative Example 3 (UNet++, that is, NestedUNet), after processing by Comparative Example 4 (TransBTS), after processing by Comparative Example 5 (UNETR).

In order to intuitively show the advantages of the disclosure, visual effect diagrams of segmentation images corresponding to Embodiment 1 and Comparative Examples 1 to 5 are provided. As shown in FIG. 3, the first column shows the original medical image, and the columns 2 to 7 show the segmentation results obtained by different models, in which white, light gray, and dark gray areas respectively represent areas of true positive, false positives, and false negative in the tumor prediction results. Notably, there is a good consistency between the tumor boundaries predicted by our method and the golden rule thereof. Also, highly similar targets in the sample of the second row can be accurately eliminated according to our method.

The embodiments are merely examples. In addition to tumors, the method and system according to the disclosure are also suitable for segmenting three-dimensional medical images of other target areas such as organs and blood vessels.

It should be understood by persons skilled in the art that the above are merely preferred embodiments according to the disclosure and are not intended to limit the disclosure. Any modifications, equivalent substitutions, and improvements made within the spirit and principles of the disclosure shall be regarded as should be included within the protection scope of the disclosure.

What is claimed is:

1. A three-dimensional medical image segmentation method based on a short-term and long-term memory self-attention model for performing segmentation on a target area image in a medical image, comprising:

(1) collecting three-dimensional medical images containing target areas and with known target area segmentation golden rules, cropping the original images according to areas of interest, and performing normalization processing on pixel values to obtain training set samples;

(2) cropping an original image according to an area of interest for an original three-dimensional medical image to be segmented, and performing a normalization operation on pixel values of the cropped image to obtain a sample to be segmented;

(3) establishing a three-dimensional medical image segmentation network based on short-term and long-term memory self-attention, wherein the network first uses a feature extraction module comprising a plurality of convolution layers, and using a convolution calculation to convert grayscale information in a network input image into feature information to obtain initial image features; using a plurality of sequentially connected convolution modules having residual structures to further process the initial image features to obtain corresponding convolution features; using a plurality of short-term memory modules based on a multi-head self-attention mechanism to calculate a global correlation between the convolution features of different levels, generating short-term memory features based on the global correlation together with the convolution features used in the correlation calculation; performing a global correlation calculation on all of the short-term memory features obtained by a long-term memory module also based on the multi-head self-attention mechanism to generate features to be reconstructed used to reconstruct a segmentation result, wherein the long-term memory module has same structure as any one of the short-term memory modules; and finally, performing processing on the features to be reconstructed through a plurality of convolution layers and deconvolution layers by a reconstruction module to obtain a predicted probability of a category to which each pixel of the network input image belongs to realize performing accurate segmentation on the target area in the three-dimensional medical image; training the established three-dimensional medical image segmentation network by using the training set samples obtained in (1) and using the corresponding segmentation golden rules as labels, so that the trained network is able to realize performing segmentation on the target area contained in the network input image; and (4) using the sample to be segmented obtained in (2) as the network input image to input to the trained three-dimensional medical image segmentation network based on short-term and long-term memory self-attention obtained in (3), and outputting a segmentation result of the target area in the sample to be segmented.

2. The three-dimensional medical image segmentation method based on the short-term and long-term memory self-attention model as claimed in claim 1, wherein the three-dimensional medical image segmentation network based on short-term and long-term memory self-attention established in (3) comprises:

the feature extraction module, configured to extract image features, wherein the feature extraction module reduces a resolution and increases a quantity of channels through two convolution calculations with a stride of 2, the network input image is converted into a multi-channel feature map, and the initial image features are obtained;

the plurality of sequentially connected convolution modules having the residual structures, used to process the initial image features to obtain the corresponding convolution features, wherein a resolution of the convolution features obtained by any one of the convolution modules is same as a resolution of the initial image features; wherein the plurality of sequentially connected convolution modules having the residual structures are specifically 4 sequentially connected convolution modules having the residual structures, which are respectively recorded as the convolution module 1, the convolution module 2, the convolution module 3, and the convolution module 4, the convolution features of different levels obtained by the convolution modules are respectively recorded as the convolution feature 1, the convolution feature 2, the convolution feature 3, and the convolution feature 4;

the plurality of short-term memory modules based on the multi-head self-attention mechanism, wherein a quantity of the short-term memory modules is a quantity of the convolution modules having the residual structures minus 1, a first-level short-term memory module corresponds to convolution modules having residual structures of first two levels, and each subsequent level of the short-term memory modules corresponds to a convolution module having the residual structure of a next level sequentially; the first-level short-term memory module is used to calculate a correlation between convolution features obtained by the convolution modules having the residual structures of the first two levels, each subsequent level of the short-term memory module is used to calculate a correlation between short-term memory features obtained by a previous-level short-term memory module and convolution features obtained by a convolution module having the residual structure of a corresponding level, and the global correlation between all of the convolution features obtained by all of the convolution modules having the residual structures is calculated; preferably, the plurality of short-term memory modules based on the multi-head self-attention mechanism are specifically 3 short-term memory modules based on the multi-head self-attention mechanism, the three short-term memory modules based on the multi-head self-attention mechanism are recorded as the short-term memory module 1, the short-term memory module 2, and the short-term memory module 3, and each of the short-term memory modules has two inputs; and the convolution feature 1 is down-sampled and input to the short-term memory module 1 with the convolution feature 2 to obtain a short-term memory feature 1, the short-term memory feature 1 is down-sampled and input to the short-term memory module 2 with the convolution feature 3 to obtain a short-term memory feature 2; and the short-term memory feature 2 is down-sampled and input to the short-term memory module 3 with the convolution feature 4 to obtain a short-term memory feature 3, wherein moreover, except for a last short-term memory module, a quantity of channels is reduced by convolution calculation for the short-term memory features obtained by each of the short-term memory modules, and is added to convolution features of a lowest level input to the short-term memory module to serve as an input of a subsequent convolution module; preferably, a sum of the short-term memory feature 1 and the convolution feature 2 is used as an input of the convolution module 3, and a sum of the short-term memory feature 2 and the convolution feature 3 is used as an input of the convolution module 4;

the long-term memory module based on the multi-head self-attention mechanism, used to first merge the short-term memory features obtained by each of the short-term memory modules in a channel dimension to generate merged features, and then perform a global correlation calculation to generate features to be reconstructed used to reconstruct the segmentation result;

wherein preferably, the long-term memory module based on the multi-head self-attention mechanism is used to first merge the short-term memory feature 1, the short-term memory feature 2, and the short-term memory feature 3 in the channel dimension to generate the merged features, and then perform a global correlation calculation on the merged features to generate the features to be reconstructed used to reconstruct the segmentation result; and the reconstruction module, used to use the features to be reconstructed as the input, use the deconvolution layer with the stride of 2 to increase the image resolution, and use the two layers of convolution layers with the stride of 1 to reduce the quantity of channels, so as to finally obtain the predicted probability of the category to which each of the pixels of the network input image belongs to.

3. The three-dimensional medical image segmentation method as claimed in claim 2, wherein the feature extraction module comprises 12 layers of detail structures, and an output of an upper layer of the detail structure is used as an input of a next layer of the detail structure, wherein a first layer is a convolution layer, a stride is 2, an output resolution is ½ of the network input image, and a quantity of output channels is a preset value;

a second layer is a batch normalization (BN) layer;

a third layer is a rectified linear unit (ReLU) activation layer;

a fourth layer is a convolution layer, a stride is 1, and a resolution of input and a quantity of channels are not changed;

a fifth layer is a batch normalization (BN) layer;

a sixth layer is a rectified linear unit (ReLU) activation layer;

a seventh layer is a convolution layer, a stride is 2, and compared with the input, an output resolution is reduced by half, and a quantity of output channels is doubled;

an eighth layer is a batch normalization (BN) layer;

a ninth layer is a rectified linear unit (ReLU) activation layer;

a tenth layer is a convolution layer, a stride is 1, and a resolution of the input and a quantity of channels are not changed;

an eleventh layer is a batch normalization (BN) layer; and a twelfth layer is a rectified linear unit (ReLU) activation layer.

4. The three-dimensional medical image segmentation method as claimed in claim 2, wherein any one of the convolution modules comprises 12 layers of detail structures, and an output of an upper layer of the detail structure is used as an input of a next layer of the detail structure, wherein a first layer is a convolution layer, a stride is 1, and a resolution of input and a quantity of channels are not changed;

a second layer is a batch normalization (BN) layer;

a third layer is a rectified linear unit (ReLU) activation layer;

a fourth layer is a convolution layer, a stride is 1, and a resolution of input and a quantity of channels are not changed;

a fifth layer is a batch normalization (BN) layer;

a sixth layer is a rectified linear unit (ReLU) activation layer, wherein an input thereof is a sum of an output of the fifth layer and an input of the first layer;

a seventh layer is a convolution layer, a stride is 1, and a resolution of the input and a quantity of channels are not changed;

an eighth layer is a batch normalization (BN) layer;

a ninth layer is a rectified linear unit (ReLU) activation layer;

a tenth layer is a convolution layer, a stride is 1, and a resolution of the input and a quantity of channels are not changed;

an eleventh layer is a batch normalization (BN) layer; and a twelfth layer is a rectified linear unit (ReLU) activation layer, wherein an input thereof is a sum of an output of the eleventh layer and an input of the seventh layer.

5. The three-dimensional medical image segmentation method as claimed in claim 2, wherein for the short-term memory module,
   in the input of the short-term memory module, for the first-level short-term memory module, the convolution features obtained by the convolution module having the residual structure at the first level is recorded as memory features, and the convolution features obtained by the convolution module having the residual structure at a second level is recorded as current features; for each subsequent level of the short-term memory module, the short-term memory features obtained by the previous level short-term memory module is recorded as memory features, and the convolution features obtained by the convolution module having the residual structure of a level corresponding to the short-term memory module is recorded as the current features;
   for any one of the short-term memory modules, for the current features thereof, a quantity of channels is doubled through a convolution calculation before input; for the memory features thereof, a convolution calculation is performed with a stride of 2 before input, while a resolution is reduced and a quantity of channels is increased; preferably, reducing the resolution specifically means reducing the resolution in half, and increasing the quantity of channels specifically means doubling the quantity of channels;
   for any one of the short-term memory modules, the current features are regarded as Query in a self-attention calculation process, and the memory features are regarded as Key and Value, so as to calculate the self-attention module in the short-term memory module, specifically:
   first, feature coding is performed respectively on the three components, Query, Key, and Value by a convolution layer, and then obtained feature codes of Query, Key, and Value are divided into a preset quantity of patches in a spatial dimension; then, an attention weight is calculated according to a sequence generated corresponding to Query and Key, and the formula is:

$$Attn = \text{Softmax}\left(\frac{Q \cdot K}{\sqrt{d}}\right)$$

wherein d is a length of a feature vector, Q and K represent a sequence corresponding to Query and Key respectively, Softmax function is applied to a dimension corresponding to the Key sequence, and Attn represents the attention weight;
   then a quantity of groups of self-attention in the attention weight is doubled through a linear layer, input to a convolution layer to perform a convolution calculation with the resolution and quantity of channels being not changed, and then the quantity of groups of self-attention is restored by using another opposite linear layer to obtain a final attention weight; finally, the final attention weight and Value are matrix multiplied, and then a result is restored to a three-dimensional feature map through an inverse sequence operation; for the three-dimensional feature map, learnable weights are pre-allocated according to the quantity of channels thereof, so that the channel corresponds to the learnable weight one-to-one, and then each of the channels of the three-dimensional feature map is multiplied by the corresponding learnable weight, thereby an overall output of the self-attention module is obtained; the learnable weight is able to automatically update through training; wherein
   the overall output of the self-attention module is added to the current features after being processed by a first LN (layer normalization) layer, the output is then passed through a feed-forward neural network and a second LN layer, and an obtained result is added to the output of the first LN layer to obtain the short-term memory features.

6. The three-dimensional medical image segmentation method as claimed in claim 2, wherein for the long-term memory module,
   first, the short-term memory features output by each of the short-term memory modules are merged in the channel dimension to obtain the merged features, the merged features are regarded as Query, Key, and Value in a self-attention calculation process, so as to calculate the self-attention module in the long-term memory module, specifically:
   first, feature coding is performed respectively on the three components, Query, Key, and Value by a convolution layer, and then obtained feature codes of Query, Key, and Value are divided into a preset quantity of patches in a spatial dimension; then, an attention weight is calculated according to a sequence generated corresponding to Query and Key, and the formula is:

$$Attn = \text{Softmax}\left(\frac{Q \cdot K}{\sqrt{d}}\right)$$

wherein d is a length of a feature vector, Q and K represent a sequence corresponding to Query and Key respectively, Softmax function is applied to a dimension corresponding to the Key sequence, and Attn represents the attention weight;
   then a quantity of groups of self-attention in the attention weight is doubled through a linear layer, input to a convolution layer to perform a convolution calculation with the resolution and quantity of channels being not changed, and then the quantity of groups of self-attention is restored by using another opposite linear layer to obtain a final attention weight; finally, the final attention weight and Value are matrix multiplied, and then a result is restored to a three-dimensional feature map through an inverse sequence operation; for the three-dimensional feature map, learnable weights are pre-allocated according to the quantity of channels thereof, so that the channel corresponds to the learnable weight one-to-one, and then each of the channels of the three-dimensional feature map is multiplied by the corresponding learnable weight, thereby an overall output of the self-attention module is obtained; the learnable weight is able to automatically update through training; wherein
   the overall output of the self-attention module is added to the current features after being processed by a first LN (layer normalization) layer, the output is then passed through a feed-forward neural network and a second LN layer, and an obtained result is added to the output of the first LN layer to obtain the short-term memory features.

7. The three-dimensional medical image segmentation method as claimed in claim 2, wherein the reconstruction module comprises 18 layers of detail structures, and an output of an upper layer of the detail structure is used as an input of a next layer of the detail structure, wherein
  a first layer is a batch normalization (BN) layer;
  a second layer is a rectified linear unit (ReLU) activation layer;
  a third layer is a convolution layer, a stride is 1, and a resolution of the input and a quantity of channels are not changed;
  a fourth layer is a batch normalization (BN) layer;
  a fifth layer is a rectified linear unit (ReLU) activation layer;
  a sixth layer is a deconvolution layer, a stride is 2, and compared with the input, an output resolution is doubled, and a quantity of output channels is not changed;
  a seventh layer is a batch normalization (BN) layer;
  an eighth layer is a rectified linear unit (ReLU) activation layer;
  a ninth layer is a convolution layer, a stride is 1, and a resolution of the input and a quantity of channels are not changed;
  a tenth layer is a batch normalization (BN) layer;
  an eleventh layer is a rectified linear unit (ReLU) activation layer;
  a twelfth layer is a deconvolution layer, a stride is 2, and compared with the input, an output resolution is doubled, and a quantity of output channels is not changed;
  a thirteenth layer is a batch normalization (BN) layer;
  a fourteenth layer is a rectified linear unit (ReLU) activation layer;
  a fifteenth layer is a convolution layer, a stride is 1, and compared with the input, an output resolution is not changed, and a quantity of output channels is reduced by half;
  a sixteenth layer is a batch normalization (BN) layer;
  a seventeenth layer is a rectified linear unit (ReLU) activation layer; and
  an eighteenth layer is a convolution layer, a stride is 1, and compared with the input, an output resolution is not changed, and a quantity of output channels is 2.

8. The three-dimensional medical image segmentation method as claimed in claim 1, wherein in (1), the training set samples further comprise performing rotation, translation, and/or flipping on the cropped images, and normalization processing is performed on the pixel values to obtain the samples, and
  the target areas are tumor areas, organ areas, or blood vessel areas.

9. A three-dimensional medical image segmentation system based on a short-term and long-term memory self-attention model, which comprises functional modules as follows:
  an image pre-processing function module, used to crop an original image according to an area of interest for an original three-dimensional medical image to be segmented, and perform a normalization operation on pixel values of the cropped image to obtain a sample to be segmented;
  a three-dimensional medical image segmentation network based on short-term and long-term memory self-attention, used to first use a feature extraction module comprising a plurality of convolution layers, and use a convolution calculation to convert grayscale information in a network input image into feature information to obtain initial image features; then use a plurality of sequentially connected convolution modules having residual structures to further process the initial image features to obtain corresponding convolution features; then use a plurality of short-term memory modules based on a multi-head self-attention mechanism to calculate a global correlation between the convolution features of different levels, and generate short-term memory features based on the global correlation together with the convolution features used in the correlation calculation; then, perform a global correlation calculation on all of the short-term memory features obtained by a long-term memory module also based on the multi-head self-attention mechanism to generate features to be reconstructed used to reconstruct a segmentation result, wherein the long-term memory module has same structure as any one of the short-term memory modules; and finally, perform processing on the features to be reconstructed through a plurality of convolution layers and deconvolution layers by a reconstruction module to obtain a predicted probability of a category to which each pixel of the network input image belongs to realize performing accurate segmentation on the target area in the three-dimensional medical image; and
  the three-dimensional medical image segmentation network based on short-term and long-term memory self-attention has been trained to use the sample to be segmented obtained from the image pre-processing function module as the network input image to input, and output the segmentation result of the target area in the sample to be segmented, wherein the training is performed by using the training set samples and using corresponding segmentation golden rules as labels, and the training set samples are obtained by collecting three-dimensional medical images containing target areas and with known target area segmentation golden rules, cropping the original images according to areas of interest, and performing normalization processing on pixel values.

10. The three-dimensional medical image segmentation system as claimed in claim 9, wherein the three-dimensional medical image segmentation network based on short-term and long-term memory self-attention specifically comprises:
  the feature extraction module, used to extract image features, wherein the feature extraction module reduces a resolution and increases a quantity of channels through two convolution calculations with a stride of 2, the network input image is converted into a multi-channel feature map, and the initial image features are obtained;
  the plurality of sequentially connected convolution modules having the residual structures, used to process the initial image features to obtain the corresponding convolution features, wherein a resolution of the convolution features obtained by any one of the convolution modules is same as a resolution of the initial image features; preferably, the plurality of sequentially connected convolution modules having the residual structures are specifically 4 sequentially connected convolution modules having the residual structures, which are respectively recorded as the convolution module 1, the convolution module 2, the convolution module 3, and the convolution module 4, the convolution features of different levels obtained by the convolution modules are respectively recorded as the convolution feature 1, the convolution feature 2, the convolution feature 3, and the convolution feature 4;

the plurality of short-term memory modules based on the multi-head self-attention mechanism, wherein a quantity of the short-term memory modules is a quantity of the convolution modules having the residual structures minus 1, a first-level short-term memory module corresponds to convolution modules having residual structures of first two levels, and each subsequent level of the short-term memory modules corresponds to a convolution module having the residual structure of a next level sequentially; the first-level short-term memory module is used to calculate a correlation between convolution features obtained by the convolution modules having the residual structures of the first two levels, each subsequent level of the short-term memory module is used to calculate a correlation between short-term memory features obtained by a previous-level short-term memory module and convolution features obtained by a convolution module having the residual structure of a corresponding level, and the global correlation between all of the convolution features obtained by all of the convolution modules having the residual structures is calculated; preferably, the plurality of short-term memory modules based on the multi-head self-attention mechanism are specifically 3 short-term memory modules based on the multi-head self-attention mechanism, the three short-term memory modules based on the multi-head self-attention mechanism are recorded as the short-term memory module 1, the short-term memory module 2, and the short-term memory module 3, and each of the short-term memory modules has two inputs; and the convolution feature 1 is down-sampled and input to the short-term memory module 1 with the convolution feature 2 to obtain a short-term memory feature 1, the short-term memory feature 1 is down-sampled and input to the short-term memory module 2 with the convolution feature 3 to obtain a short-term memory feature 2; and the short-term memory feature 2 is down-sampled and input to the short-term memory module 3 with the convolution feature 4 to obtain a short-term memory feature 3, wherein moreover, except for a last short-term memory module, a quantity of channels is reduced by convolution calculation for the short-term memory features obtained by each of the short-term memory modules, and is added to convolution features of a lowest level input to the short-term memory module to serve as an input of a subsequent convolution module; preferably, a sum of the short-term memory feature 1 and the convolution feature 2 is used as an input of the convolution module 3, and a sum of the short-term memory feature 2 and the convolution feature 3 is used as an input of the convolution module 4;

the long-term memory module based on the multi-head self-attention mechanism, used to first merge the short-term memory features obtained by each of the short-term memory modules in a channel dimension to generate merged features, and then perform a global correlation calculation to generate features to be reconstructed used to reconstruct the segmentation result; wherein preferably, the long-term memory module based on the multi-head self-attention mechanism is used to first merge the short-term memory feature 1, the short-term memory feature 2, and the short-term memory feature 3 in the channel dimension to generate the merged features, and then perform a global correlation calculation on the merged features to generate the features to be reconstructed used to reconstruct the segmentation result; and the reconstruction module, used to use the features to be reconstructed as the input, use the deconvolution layer with the stride of 2 to increase the image resolution, and use the two layers of convolution layers with the stride of 1 to reduce the quantity of channels, so as to finally obtain the predicted probability of the category to which each of the pixels of the network input image belongs to.

* * * * *